United States Patent [19]

Drake

[11] Patent Number: 4,868,309

[45] Date of Patent: Sep. 19, 1989

[54] SEPARATION OF ALKENYLPYRIDINES FROM ALKYLPYRIDINES

[75] Inventor: Charles A. Drake, Nowata, Okla.

[73] Assignee: Phillips Petroleum Company, Bartlesville, Okla.

[21] Appl. No.: 213,969

[22] Filed: Jul. 1, 1988

[51] Int. Cl.[4] ................ C07D 213/06; C07D 213/127
[52] U.S. Cl. ..................................... 546/350; 546/353
[58] Field of Search ................................ 546/353, 350

[56] References Cited

U.S. PATENT DOCUMENTS

| | | | |
|---|---|---|---|
| 2,716,120 | 8/1955 | Haskell | 546/350 |
| 2,879,272 | 3/1959 | Pennington | 260/397.3 |
| 3,431,266 | 3/1969 | Masciantonio et al. | 546/353 |
| 4,429,170 | 1/1984 | Lovell | 568/761 |

Primary Examiner—Alan L. Rotman
Attorney, Agent, or Firm—K. K. Brandes

[57] ABSTRACT

In a countercurrent extraction process for extracting at least one alkylpyridine (preferably 2-methyl-5-ethylpyridine) from a liquid feed stream also comprising at least one alkylenepyridine (preferably 2-methyl-5-vinylpyridine) by means of an aqueous acid solution (preferably aqueous $H_2SO_4$), the improvement comprises the presence of a gas stream, preferably flowing in the same direction as the liquid feed stream.

10 Claims, No Drawings

SEPARATION OF ALKENYLPYRIDINES FROM ALKYLPYRIDINES

BACKGROUND OF INVENTION

This invention relates to a process for separating alkenylpyridines from alkylpyridines by liquid-liquid extraction with an aqueous solution of an acid.

The separation of alkenylpyridines (in particular 2-methyl-5-vinylpyridine) from alkylpyridines (in particular 2-methyl-5-ethylpyridine) by countercurrent extraction with aqueous acid solutions is known and has been described in U.S. Pat. Nos. 2,716,120 and 2,879,272. However, there is an ever present need to improve the separation effectiveness of these processes.

SUMMARY OF THE INVENTION

It is a object of this invention to modify the countercurrent extraction of mixtures comprising alkenylpyridines and alkylpyridines with aqueous acidic solutions so as to enhance the selectivity to alkenylpyridines. Additional objects and advantages of this invention will be apparent from the disclosure and the appended claims.

According to this invention, in a process for contacting (i) a liquid feed stream comprising at least one alkenylpyridine and at least one alkylpyridine countercurrently with (ii) an extractant solution comprising water and at least one acid, under such contacting conditions in a contacting zone as to obtain (ii) a liquid product stream (raffinate stream) containing more alkenylpyridine and less alkylpyridine than said liquid feed stream, and (iv) an extract stream comprising water, said acid and alkylpyridine (i.e., at least a portion of alkylpyridine contained in the liquid feed); the improvement comprises passing a gas stream through said contacting zone during said contacting.

Preferably, the flow direction of the gas stream is the same as the direction of the liquid feed stream comprising at least one alkenylpyridine and at least one alkylpyridine.

The introduction of the gas stream is carried out under such conditions as to enhance the separation fo alkenylpyridine and alkylpyridine (as compared with the separation without the gas stream), i.e., the concentration of alkenylpridine in the raffinate is higher when a gas stream is used in the countercurrent extraction process than in such process without the gas stream.

In a more preferred embodiment, the at least one alkenylpyridine is 2-methyl-5-vinylpyridine, the at least one alkylpyridine is 2-methyl-5-ethylpyridine, and the at least one acid is sulfuric acid. The gas stream preferably is a stream of $H_2$ or $N_2$ (or a mixture of both). More preferably, the volume ratio of the gas to the liquid feed is in the range of from about 2:1 to about 20:1.

DETAILED DESCRIPTION OF THE INVENTION

Any feed stream containing at least one alkenylpyridine and at least one alkylpyridine can be employed in the process of this invention. Preferred are alkenylpyridines containing at least one alkenyl group of 2-10 carbon atoms per group, and alkylpyridines containing at least one alkyl group of 2-10 carbon atoms per group. Non-limiting examples of suitable alkenylpyridines and suitable alkylpyridines are cited in U.S. Pat. Nos. 2,716,120 and 2,879,212, the disclosures of which are herein incorporated by reference. The presently more preferred alkenylpyridine is 2-methyl-5-vinylpyridine, and the presently preferred alkylpyridine is 2-methyl-5-ethylpyridine.

The liquid feed stream can be derived from any source, and can contain any weight percentage of alkenylpyridine (preferably about 40–98 weight-%) and any weight percentage of alkylpyridine (preferably about 60–2 weight-%). It is understood that the feed stream can contain minor amounts of other materials such as hydrocarbons, unsubstituted pyridine, picolines, and the like, as are recited in U.S. Pat. No. 2,716,120.

Any suitable aqueous solution of at least one mineral acid (inorganic acid) can be employed. A non-limiting list of suitable mineral acids is recited in U.S. Pat. Nos. 2,716,120 and 2,879,272, and includes acid salts as well as inorganic and organic acids. The presently preferred acid is $H_2SO_4$.

Any suitable concentration of the acid in the aqueous contacting solution can be employed, and the pH can be in the range of from about 6 to about 0. In a preferred embodiment, the aqueous contacting solution has a pH in the range of from about 3 to 0. In a more preferred embodiment, an aqueous solution containing about 0.5 to about 2 weight-% of the acid (most preferably $H_2SO_4$) is employed.

Any suitable gas can be utilized in the process of this invention, as long as the gas does not react with the alkenylpyridine and/or the alkylpyridine. Suitable gases includes $H_2$, $N_2$, He, Ne, Ar, Kr, methane, ethane, propane, and the like. Presently preferred are $H_2$, $N_2$, and mixtures of $H_2$ and $N_2$.

Any suitable volume ratio of the aqueous acid extractant solution to the liquid feed (containing alkenyl- and alkylpyridines) can be employed. Preferably, the volume ratio of extractant solution to liquid feed stream is in the range of from about 3:1 to about 15:1, more preferably from about 6:1 to about 10:1. Any suitable volume ratio of the gas to the liquid feed can be employed. The gas:feed volume ratio preferably is in the range of from about 2:1 to about 20:1, more preferably from about 6:1 to about 15:1, most preferably about 12:1 to about 15:1.

Any suitable apparatus can be used for the contacting process (i.e., extraction process) of this invention. Generally, an extraction column is used, with the liquid feed and the gas being introduced at or near the bottom of the column, and the acidic extractant solution being introduced above the points of entrance of liquid feed and gas (preferably near the top of the column). Thus, liquid feed and gas flow upwardly, and the extractant solution flows downwardly through the column. Suitable locations for introducing feed and extractant in extraction processes are indicated in U.S. Pat. Nos. 2,716,120, and 2,879,272.

Any suitable extraction column can be utilized in the process of this invention. Most common are packed columns, i.e., columns packed with glass or ceramic bodies, e.g., Raschig rings. Other suitable columns are perforated plate columns, rotary-agitated columns, vibrating-plate columns, and others known to those of ordinary skill in the liquid-liquid extraction technology. The specific dimensions of the columns can be determined by those skilled in the art and will depend on flow rates of liquid feed, aqueous extractant solution and gas, on the desired separation efficiency, and the like.

It is generally preferred to recover the alkylpyridine from the aqueous acidic extract stream. This can be accomplished by any suitable liquid-liquid separation technique, such as fractional distillation. The raffinate (product) stream containing the alkenylpyridine can be purified further, if desired, e.g,. by repeating the extraction process of this invention once or more than once. The raffinate stream can be dried by any suitable desiccant, such as silica gel. The alkenylpyridine can be recovered from the product stream by any suitable separation technique, e.g., distillation.

The following examples are presented to further illustrate the invention and are not to be construed as unduly limiting the scope of the invention.

EXAMPLE I

This example illustrates the experimental set-up for separating 2-methyl-5-vinylpyridine (MVP) from 2-methyl-5-ethylpyridine (MEP) in accordance with the process of this separation.

A glass tube, which was about 20 inches high, had an inner diameter of about 0.5 inches and was filled with stainless steel rings, was used as the extraction column. An aqueous solution of 1.5 weight-% $H_2SO_4$ was introduced through an inlet tube at the top of the column. This inlet tube extended about 2 inches into the packed extraction column. A combined stream of a gas ($N_2$ or $H_2$) and of a crude liquid feed containing about 56 weight-% MVP and about 24 weight-% MEP was introduced through an inlet tube at the bottom of the column. The bottom inlet tube extended about 2 inches into the packed extraction column. A raffinate steam containing more MPV than the feed stream exited through an outlet tube at the top of the column (at a location above the lower opening of the inlet tube for aqueous $H_2SO_4$); and the extract stream (i.e., aqueous $H_2SO_4$ + EVP) exited at the bottom of the column (at a location below the upper opening of the inlet tube for the gas/MVP/MEP feed).

The flow rate of the liquid MVP/EVP feed stream (flowing upwardly through the packed column) was in the range of about 0.75 to about 1.5 cc/minute. The flow rate of the gas (flowing upwardly through the packed column concurrently with the MVP/MEP stream) was about 10 cc/minute. The flow rate of the 1.5 weight-% aqueous $H_2SO_4$ extractant (flowing downwardly through the packed column) was about 8 cc/minute.

The temperature during the extraction process was about 25° C. ($\pm 5°$ C.). The analysis of feed and raffinate streams was carried out, at intervals of about 2 hours, by gas chromatography, employing a Hewlett-Packard 5890 gas chromatograph and a SE-30 silicone column (10 ft. high; ⅛ inch diameter).

EXAMPLE II

This example illustrates the effect of a gaseous co-feed on the separation efficiency in the extraction process described in Example I. Test results are summarized in Table I.

TABLE I

| Run | Gas Employed | Flow Rates (cc/minute) | | | Volume Ratio of Gas to Feed | Raffinate Composition | |
|---|---|---|---|---|---|---|---|
| | | $H_2SO_4$ Solution | MVP/MEP Feed | Gas | | Wt-% MVP | Wt-% MEP |
| 1 (Control) | None | 8 | 0.75 | 0 | 0 | 64 | 24 |
| 2 (Invention) | $N_2$ | 8 | 0.75 | 10 | 13.3:1 | 91 | 4 |
| 3 (Invention) | $H_2$ | 8 | 0.75 | 10 | 13.3:1 | 90 | 6 |
| 4 (Control) | None | 8 | 1.5 | 0 | 0 | 64 | 24 |
| 5 (Invention) | $N_2$ | 8 | 1.5 | 10 | 6.7:1 | 86 | 11 |
| 6 (Invention) | $H_2$ | 8 | 1.5 | 10 | 6.7:1 | 86 | 11 |

Test results in Table I show that the separating of MVP and MEP was significantly enhanced when a gas was used as a co-feed, in particular at a gas:feed volume ratio of about 13:1. The test data further show that doubling of the volume ratio of the $H_2SO_4$ extractant to the liquid feed had essentially no effect on the separation efficienty (compare Run 4 with Run 1), while doubling of the volume ratio of the gas to the liquid feed resulted in a 50% reduction in MEP concentration in the raffinate (compare Runs 2 and 3 with Runs 5 and 6). These results are quite surprising.

Reasonable variations, modifications and adaptations for various usages and conditions can be made within the scope of the disclosure and the appended claims, without departing from the scope of this invention.

That which is claimed is:

1. In a process for contacting (i) a liquid feed stream comprising 2-methyl-5-vinylpyridine and 2-methyl-5-ethylpyridine countercurrently with (ii) an aquous extractant solution having a pH of about 0 to about 6, under such contacting conditions in a contacting zone as to obtain (iii) a liquid product stream containing more 2-methyl-5-vinylpyridine and less 2-methyl-5-ethylpyridine than said liquid feed stream and (iv) an extract stream comprising said extractant solution and at least a portion of said 2-methyl-5-ethylpyridine contained in said liquid feed stream;

the improvement which comprises passing gas stream through said contacting zone during said contacting, wherein said gas stream does not react with said 2-methyl-5-vinylpyridine and said 2-methyl-5-ethylpyridine.

2. A process in accordance with claim 1, wherein the flow direction of said gas stream is the same as the flow direction of said liquid feed stream.

3. A process in accordance with claim 1, wherein said liquid feed stream and said gas stream flow upwardly through said contacting zone, and said extractant solution flows downwardly through said contacting zone.

4. A process in accordance with claim 1, wherein said liquid feed stream contains about 40–98 weight percent 2-methyl-5-vinylpyridine and about 60–2 weight percent 2-methyl-5-ethylpyridine.

5. A process in accordance with claim 1, wherein the gas in said gas stream is selected from the group consisting of nitrogen, hydrogen, and mixtures of nitrogen and hydrogen.

6. A process in accordance with claim 1, wherein said extractant solution is an aqueous solution of sulfuric acid having a pH of about 0–3.

7. A process in accordance with claim 6, wherein said extractant solution contains about 0.5 to about 2 weight percent $H_2SO_4$.

8. A process in accordance with claim 1, wherein the volume ratio of said gas stream to said liquid feed stream is in the range of from about 2:1 to about 20:1.

9. A process in accordance with claim 1, wherein the volume ratio of said extractant solution to said liquid feed stream is in the range of from about 3:1 to about 15:1.

10. A process in accordance with claim 1 comprising the additional steps of recovering 2-methyl-5-vinylpyridine from said liquid product stream (iii) and recovering 2-methyl-5-ethylpyridine from said extract stream (iv).

* * * * *